United States Patent [19]

King et al.

[11] Patent Number: 5,220,069

[45] Date of Patent: Jun. 15, 1993

[54] PROCESSES FOR THE PREPARATION OF CARBAMATES

[75] Inventors: Stephen W. King, Scott Depot; Bernard C. Ream, Charleston, both of W. Va.

[73] Assignee: Union Carbide Chemicals & Plastics Technology Corporation, Danbury, Conn.

[21] Appl. No.: 585,456

[22] Filed: Sep. 20, 1990

[51] Int. Cl.$^5$ .......................................... C07C 209/00
[52] U.S. Cl. .................... 564/393; 560/345; 564/468
[58] Field of Search ............... 560/330, 345; 564/393, 564/468, 507

[56] References Cited

U.S. PATENT DOCUMENTS

| | | | |
|---|---|---|---|
| 2,713,591 | 7/1955 | Bortnick | 560/345 |
| 3,366,662 | 1/1968 | Kober et al. | 560/345 |
| 3,763,217 | 2/1973 | Brill | 560/25 |
| 4,081,472 | 3/1978 | Tsumura et al. | 560/345 |

OTHER PUBLICATIONS

Mar., *Advanced Organic Chemistry: Reactions, Mechanisms, and Structure*, (1968), pp. 435-436, 477-480 and 878-879.

Dow Chemical U.S.A., *Experimental Ethylene Carbonate XAS-1666.00L,* Product Bulletin (1982), pp. 5-7, No. 116-1037-82.

Trotta et al., *J. Org. Chem.*, (1987), vol. 52, No. 7, pp. 1300-1304.

Chemical Abstracts, vol. 107, No. 18, Nov. 22, 1987, p. 154, abstract No. 156950y, Columbus, Ohio, US.

*Primary Examiner*—José G. Dees
*Assistant Examiner*—Vera C. Clarke
*Attorney, Agent, or Firm*—R. M. Allen

[57] ABSTRACT

A process for preparing nitrogen-containing compounds which comprises contacting a carboxylated N-monosubstituted nitrogen-containing compound or a carboxylated N,N-disubstituted nitrogen-containing compound with a mixed metal oxide catalyst under conditions effective to produce the nitrogen-containing compound.

26 Claims, No Drawings

PROCESSES FOR THE PREPARATION OF CARBAMATES

RELATED APPLICATIONS

The following are related, commonly assigned applications, filed on an even date herewith:

U S. patent application Ser. No. 07/585,561; U.S. patent application Ser. No. 07/585,560, now abandoned; U.S. patent application Ser. No. 07/585,455; U.S. patent application Ser. No. 07/585,563; U.S. patent application Ser. No. 07/585,564, now abandoned; U.S. patent application Ser. No. 07/585,559; U.S. patent application Ser. No. 07/585,565; U.S. Pat. No. 5,104,987, granted Apr. 14, 1992; and U.S. patent application Ser. No. 07/585,556, now U.S. Pat. No. 5,164,497; all of which are incorporated herein by reference.

BRIEF SUMMARY OF THE INVENTION

1. Technical Field

This invention relates to a process for preparing nitrogen-containing compounds which comprises contacting a carboxylated N-monosubstituted nitrogen-containing compound or a carboxylated N,N-disubstituted nitrogen-containing compound with a mixed metal oxide catalyst under conditions effective to produce the nitrogen-containing compound.

2. Background of the Invention

Decarboxylation, that is, elimination of the —COOH group as $CO_2$, is a known process. March, J., Advanced Organic Chemistry: Reactions, Mechanisms, and Structure, 1968, pp. 435–436, 477–480 and 878–879, describes various decarboxylation reactions. At pages 435–436, it is stated that aromatic acids can be decarboxylated by heating with copper and quinoline. At pages 477–480, it is stated that aliphatic acids which undergo successful decarboxylation have certain functional groups or double or triple bonds in the alpha or beta positions such as malonic acids, alpha-cyano acids, alpha-nitro acids, alpha-aryl acids, alpha-keto acids, alpha-trihalo acids, beta-keto acids, beta,gamma-olefinic acids and the like. At pages 878–879, oxidative decarboxylation is described in which lead tetraacetate cleaves carboxyl groups, replacing them with acetoxy groups, which may be hydrolyzed to hydroxyl groups. It is stated that compounds containing carboxyl groups on adjacent carbons (succinic acid derivatives) can be bisdecarboxylated with lead tetraacetate. It is also stated that compounds containing geminal carboxyl groups (malonic acid derivatives) can be bisdecarboxylated with lead tetraacetate, gem-diacetates (acylals) being produced, which are hydrolyzable to ketones.

Enichem Synthesis SpA, Dimethyl Carbonate Product Bulletin, pp. 10–13, discloses the reaction of aromatic amines with dimethyl carbonate to give N-methyl and N,N'-dimethyl aromatic amines. It is stated that the reaction is carried out under the same conditions as used for the methylation of phenols. The reaction of phenols with dimethyl carbonate is carried out in the presence of a basic catalyst such as NaOH, $Na_2CO_3$, $NaOCH_3$, tertiary amines and heterocyclic nitrogenous compounds. Reaction temperatures of at least 140° C. are required. It is also stated that the speed of reaction can be accelerated with catalytic quantities of organic and inorganic halides. At page 12, it is stated that dimethyl carbonate reacts with amines (aliphatic or aromatic, primary or secondary) to produce carbamates and ureas. Also at page 12, it is stated that it is possible to obtain isocyanates from carbamates with a pyrolysis reaction. At page 13, it is stated that aminoalcohols can react with dimethyl carbonate in the presence of sodium or potassium alkoxides to yield 2-oxazolidinones.

Dow Chemical U.S.A., Experimental Ethylene Carbonate XAS-1666.00L Product Bulletin (1982), pp. 5–7, discloses that aromatic amines can be reacted with ethylene carbonate to form N-(2-hydroxyethyl) derivatives. It is stated that with primary amines such as aniline, a mixture of mono- and di-substituted derivatives can be prepared. It is also stated that carbamates and imidazolidinones can be produced through the reaction of ethylene carbonate with aliphatic mono- and di-amines.

Texaco Chemical Company, TEXACAR® Ethylene and Propylene Carbonates Product Bulletin (1987), pp 22–23, describes the reaction of ethylene carbonate and propylene carbonate with primary and secondary aliphatic amines at low temperatures to yield carbamates. It is stated that ethylene carbonate and propylene carbonate can react with amines to give the corresponding hydroxyethyl and hydroxypropyl derivatives.

Trotta, F. et al., J. Org. Chem., 1987, 52, pp. 1300–1304, relates to selective mono-N-alkylation of aromatic amines by dialkyl carbonate under gas-liquid phase-transfer catalysis conditions (continuous flow process). The catalyst is a polyethylene glycol in the presence of a base ($K_2CO_3$).

DISCLOSURE OF THE INVENTION

This invention relates to a process for preparing nitrogen-containing compounds which comprises contacting a carboxylated N-monosubstituted nitrogen-containing compound or a carboxylated N,N-disubstituted nitrogen-containing compound with a mixed metal oxide catalyst under conditions effective to produce the nitrogen-containing compound.

This invention also relates to a process for preparing nitrogen-containing compounds which comprises contacting ammonia or a N-monosubstituted nitrogen-containing compound with a $CO_2$ synthon in the presence of a mixed metal oxide catalyst under conditions effective to produce the nitrogen-containing compound.

This invention further relates to a process for preparing nitrogen-containing compounds which comprises (i) contacting ammonia with a $CO_2$ synthon under conditions effective to produce a carboxylated N-monosubstituted nitrogen-containing compound, and (ii) contacting the carboxylated N-monosubstituted nitrogen-containing compound with a mixed metal oxide catalyst under conditions effective to produce the nitrogen-containing compound.

This invention yet further relates to a process for preparing nitrogen-containing compounds which comprises (i) contacting a N-monosubstituted nitrogen-containing compound with a $CO_2$ synthon under conditions effective to produce a carboxylated N,N-disubstituted nitrogen-containing compound, and (ii) contacting the carboxylated N,N-disubstituted nitrogen-containing compound with a mixed metal oxide catalyst under conditions effective to produce the nitrogen-containing compound.

The nitrogen-containing compounds produced in accordance with the processes of this invention include isocyanates, N-monosubstituted nitrogen-containing compounds and N,N-disubstituted nitrogen-containing compounds which are useful for a wide variety of applications such as solvents, liquid absorbents, catalysts, acid scavengers, polyurethane reactants and the like. Selective N-monoalkylation of nitrogen-containing compounds is a preferred embodiment of this invention.

For purposes of this invention, the chemical elements are identified in accordance with the Periodic Table of the Elements, CAS version, Handbook of Chemistry and Physics, 67th Ed., 1986–87, inside cover. Also, for purposes of this invention, Group IIIB metal oxides embraces the lanthanides and actinides. As used herein, the term "oxide" embraces oxides, hydroxides and/or mixtures thereof. Also, as used herein, the term "$C_2$ synthon" embraces $SO_2$ synthons such as sulfurous acids and sulfurous acid esters.

DETAILED DESCRIPTION

As indicated above, this invention relates to a process for preparing nitrogen-containing compounds which comprises contacting a carboxylated N-monosubstituted nitrogen-containing compound or a carboxylated N,N-disubstituted nitrogen-containing compound with a mixed metal oxide catalyst under conditions effective to produce the nitrogen-containing compound.

As also indicated above, this invention relates to a process for preparing nitrogen-containing compounds which comprises contacting ammonia or a N-monosubstituted nitrogen-containing compound with a $CO_2$ synthon in the presence of a mixed metal oxide catalyst under conditions effective to produce the nitrogen-containing compound.

As further indicated above, this invention relates to a process for preparing nitrogen-containing compounds which comprises (i) contacting ammonia with a $CO_2$ synthon under conditions effective to produce a carboxylated N-monosubstituted nitrogen-containing compound, and (ii) contacting the carboxylated N-monosubstituted nitrogen-containing compound with a mixed metal oxide catalyst under conditions effective to produce the nitrogen-containing compound.

As yet further indicated above, this invention relates to a process for preparing nitrogen-containing compounds which comprises (i) contacting a N-monosubstituted nitrogen-containing compound with a $CO_2$ synthon under conditions effective to produce a carboxylated N,N-disubstituted nitrogen-containing compound, and (ii) contacting the carboxylated N,N-disubstituted nitrogen-containing compound with a mixed metal oxide catalyst under conditions effective to produce the nitrogen-containing compound.

When ammonia or a N-monosubstituted nitrogen-containing compound and a $CO_2$ synthon are employed as starting materials, it is believed that a transesterification reaction followed by a decarboxylation reaction or an elimination reaction occurs to provide the desired nitrogen-containing compound product. The occurrence of either a decarboxylation reaction or an elimination reaction is believed to be effected by the choice of $CO_2$ synthon, substituents on the N-monosubstituted nitrogen-containing compound, temperature and diluents. The exact reaction mechanism is not fully appreciated but what is appreciated is that ammonia or a N-monosubstituted nitrogen-containing compound starting material and $CO_2$ synthon starting material can be contacted in the presence of a mixed metal oxide catalyst under conditions described herein to provide a nitrogen-containing compound product. It is also appreciated that a carboxylated N-monosubstituted nitrogen-containing compound or a carboxylated N,N-disubstituted nitrogen-containing compound can be contacted with a mixed metal oxide catalyst under conditions described herein to provide a nitrogen-containing compound product.

As indicated above, selective N-monoalkylation of nitrogen-containing compounds is a preferred embodiment of this invention. When selective N-monoalkylation is desired, a molar excess of ammonia or N-monosubstituted nitrogen-containing compound relative to the $CO_2$ synthon is employed, i.e., preferably a molar ratio of from about 2:1 to about 10:1.

Step (i) of certain processes of this invention can in general be referred to as a transesterification reaction. Any suitable transesterification catalyst can be employed in step (i). Such transesterification catalysts are known and include, for example, basic metal oxides, alkoxides and other basic metal salts such as potassium carbonate, sodium titanate and the like. Other suitable transesterification catalysts include, for example, Bronsted acids such as sulfuric acid and Lewis acids such as aluminum triisopropoxide. As discussed hereinafter in regard to the decarboxylation catalyst and the catalyst used in the elimination reaction, the transesterification catalyst employed in this invention likewise may also contain support(s), binding agent(s) or other additives to stabilize or otherwise help in the manufacture of the catalyst. Both homogeneous and heterogeneous catalysts can be employed in the step (i) reaction. The amount of transesterification catalyst used in step (i) is dependent on the particular catalyst employed and can range from about 0.01 weight percent or less to about 10 weight percent or greater of the total weight of the starting materials.

Suitable N-monosubstituted nitrogen-containing compound starting materials which can be employed in the step (i) transesterification reaction include any permissible N-monosubstituted nitrogen-containing compound(s) such as those embraced by the formula $RNH_2$ wherein R is the residue of an organic compound. Preferred N-monosubstituted nitrogen-containing compound starting materials include N-monosubstituted acyclic and cyclic compounds such as alkylamines and cycloalkylamines. Illustrative N-monosubstituted nitrogen-containing compound starting materials useful in this invention include, for example, methylamine, ethylamine, cyclohexylamine, aniline, isopropylamine, ethylenediamine, monoethanolamine and the like. The molar ratio of ammonia or N-monosubstituted nitrogen-containing compound to $CO_2$ synthon is not narrowly critical and can range from about 0.05:1 or less to about 50:1 or greater, preferably from about 0.1:1 to about 10:1. However, when selective N-monoalkylation is desired, a molar excess of ammonia or N-monosubstituted nitrogen-containing compound relative to the $CO_2$ synthon is employed, i.e., preferably a molar ratio of from 2:1 to about 10:1.

Suitable $CO_2$ synthon starting materials which can be employed in the step (i) transesterification reaction include any permissible substituted or unsubstituted carboxyl-containing compound(s) or carbonyl-containing compound(s) which are capable of reacting with ammonia or a N-monosubstituted nitrogen-containing compound under the process of conditions described herein, such as those embraced by the formulae $R_1C(O)R_2$ or $R_1S(O)R_2$ wherein $R_1$ is hydrogen, halogen, amino, hydroxyl or the residue of an organic compound, and $R_2$ is amino, hydroxyl or the residue of an organic compound. Illustrative $CO_2$ synthons include, for example, substituted and unsubstituted carbonates, chlorocarbonates, carbonic acids, carbamates, carbamic acids, oxalates, 2-oxazolidinones, ureas, esters, phosgene, chloroformates, carbon dioxide, orthocarboxylates, sulfurous acids, sulfurous acid esters and the like. For purposes of this invention, carbon monoxide is also considered a $CO_2$ synthon for appropriate oxidative carbonylation reactions. Preferred $CO_2$ synthons include, for example, diphenyl carbonate, ethylene carbonate, dimethyl carbonate, 2-oxazolidinone, urea, substituted urea, ethylene sulfite and the like. The use of $CO_2$ synthons prepared in situ such as the reaction of ethylene carbonate and monoethanolamine to give 2-oxazolidinone is encompassed within the scope of this invention.

As indicated above, $R_1$ and $R_2$ can be the residue of an organic compound. Illustrative residues of organic compounds include, for example, alkyl, aryl, alkylamino, arylamino, cycloalkyl, heterocycloalkyl, alkyloxy, aryloxy, cycloalkyloxy, heterocycloalkyloxy, alkyloxycarbonyl, aryloxycarbonyl, cycloalkyloxycarbonyl, heterocycloalkyloxycarbonyl, hydroxycarbonyl and the like. Additionally, for purposes of defining the $CO_2$ synthon by the formulae above, the $R_1$ and $R_2$ substituents together can complete a cycloalkyl ring or a heterocycloalkyl ring which can be substituted or unsubstituted. The $R_1C(O)R_2$ formula is also contemplated to embrace carbon dioxide and carbon monoxide.

The step (i) transesterification reaction can be conducted over a wide range of pressures ranging from atmospheric or subatmospheric pressures to superatmospheric pressures. However, the use of very high pressures has not been observed to confer any significant advantages but increases equipment costs. Further, it is preferable to conduct the step (i) reaction at reduced pressures of from about 1 mm Hg to less than about 760 mm Hg. The step (i) transesterification reaction is preferably effected in the liquid or vapor states or mixtures thereof.

The temperature of the step (i) transesterification reaction may be as low as about ambient temperature to about 300° C. Preferably, the reaction temperature ranges from about 50° C. to about 200° C., and most preferably from about 60° C. to about 120° C.

Suitable carboxylated N-monosubstituted nitrogen-containing compounds prepared by the step (i) transesterification reaction include any permissible carboxylated N-monosubstituted nitrogen-containing compounds which are capable of eliminating carbon dioxide under the process conditions described herein, such as those embraced by the formulae $H_2N(C(O)OR_1)$ or $H_2N(C(O)OR_2)$ wherein $R_1$ and $R_2$ are as defined above. Illustrative carboxylated N-monosubstituted nitrogen-containing compounds include, for example, methyl carbamate, ethyl carbamate, isopropyl carbamate and the like. The amount of carboxylated N-monosubstituted nitrogen-containing compound(s) employed in step (ii) is dependent on the amount of mixed metal oxide catalyst employed.

Suitable carboxylated N,N-disubstituted nitrogen-containing compounds prepared by the step (i) transesterification reaction include any permissible carboxylated N,N-disubstituted nitrogen-containing compounds which are capable of eliminating carbon dioxide under the process conditions described herein, such as those embraced by the formula $RHN(C(O)OR_1)$ or $RHN(C(O)OR_2)$ wherein R, $R_1$ and $R_2$ are as defined above. Illustrative carboxylated N,N-disubstituted nitrogen-containing, compounds include, for example, methyl N-methyl carbamate, ethyl N-ethyl carbamate and the like. The amount of carboxylated N,N-disubstituted nitrogen-containing compound(s) employed in step (ii) is dependent on the amount of mixed metal oxide catalyst employed.

The carboxylated N-monosubstituted nitrogen-containing compounds and carboxylated N,N-disubstituted nitrogen-containing compounds prepared by the step (i) transesterification reaction may undergo one or more transesterifications prior to the step (ii) reaction. For example, a hydroxyl-containing compound may be reacted with the originally prepared carboxylated N-monosubstituted nitrogen-containing compound or carboxylated N,N-disubstituted nitrogen-containing compound under conditions effective to prepare a different carboxylated N-monosubstituted nitrogen-containing compound or a different carboxylated N,N-disubstituted nitrogen-containing compound. Suitable hydroxyl-containing compounds include those embraced by the formula $R_3OH$ wherein $R_3$ is the residue of an organic compound. This invention is not intended to be limited in any manner by the step (i) transesterification reaction.

Step (ii) of certain processes of this invention can in general be referred to as a decarboxylation reaction or an elimination reaction. Suitable catalysts which can be employed in step (ii) include two or more metal oxides. A magnesium:aluminum mixed metal oxide is a preferred mixed metal oxide catalyst as more fully described below. Both homogeneous and heterogeneous catalysts can be employed in the step (ii) reaction. The amount of metal oxide catalyst used in step (ii) is not narrowly critical and is dependent on whether step (ii) is conducted batchwise or continuously. If batchwise, the catalyst employed can range from about 0.01 weight percent or less to about 10 weight percent or greater of the total weight of the starting materials. If continuously, generally a fixed bed is employed.

Suitable mixed metal oxide catalysts for use in the processes of this invention comprise mixed metal oxides containing two or more metal oxides. Illustrative of such mixed metal oxides include, for example, two or more of the following: Group IA metal oxides, Group IIA metal oxides, Group IIIB metal oxides (including lanthanides and actinides), Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides. Certain of these metal oxide(s) may also be used as transesterification catalysts in accordance with this invention such as Group IIA and/or IIIA metal oxides. Preferred mixed metal oxides are amphoteric or basic. Preferred mixed metal oxides which may be utilized as decarboxylation catalysts include, for example, two or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

Group IIA metal oxides such as magnesium oxide and calcium oxide and Group IIIA metal oxides such as aluminum oxide and gallium oxide are preferred mixed metal oxides for use in this invention. For mixed metal oxides in which at least one of the metals is magnesium, suitable metals in association with magnesium may include, for example, one or more of the following: Group IIIA metals such as boron, aluminum, gallium and indium, Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IVA metals such as silicon, germanium, tin and lead, Group VA metals such as arsenic, antimony and bismuth, and Group IVB metals such as zirconium and hafnium For mixed metal oxides in which at least one of the metals is calcium, suitable metals in association with calcium may include, for example, one or more of the following: Group IIIA metals such as boron, aluminum, gallium and indium, Group IVA metals such as silicon, germanium, tin and lead, Group VB metals such as niobium and tantalum, and Group VIB metals such as chromium, molybdenum and tungsten.

Illustrative of mixed metal oxides which may be used as catalysts include, for example, $MgO—Al_2O_3$, $MgO—SiO_2$, $MgO—CdO$, $MgO—Bi_2O_3$, $MgO-Sb_2O_5$, $MgO—SnO_2$, $MgO—ZrO_2$, $MgO—BeO$, $MgO—TiO_2$, $MgO—CaO$, $MgO—SrO$, $MgO—ZnO$, $MgO—Ga_2O_3$, $MgO—Y_2O_3$, $MgO—La_2O_3$, $MgO—MoO_3$, $MgO—Mn_2O_3$, $MgO—Fe_2O_3$, $MgO—Co_3O_4$, $MgO—WO_3$, $MgO—V_2O_5$, $MgO—Cr_2O_3$, $MgO—ThO_2$, $MgO—Na_2O$, $MgO—BaO$, $MgO—CaO$, $MgO—HfO_2$, $MgO—Li_2O$, $MgO—Nb_2O_5$, $MgO—Ta_2O_5$, $MgO—Gd_2O_3$, $MgO—Lu_2O_3$, $MgO—Yb_2O_3$, $MgO—CeO_2$, $MgO—Sc_2O_3$, $MgO—PbO$, $MgO—NiO$, $MgO—CuO$, $MgO—CoO$, $MgO—B_2O_3$, $CaO-SiO_2$, $CaO-Al_2O_3$, $CaO—SnO$, $CaO—PbO$, $CaO—Nb_2O_5$, $CaO-Ta_2O_5$, $CaO—Cr_2O_3$, $CaO—MoO_3$, $CaO—WO_3$, $CaO—TiO_2$, $CaO—HfO_2$, $MgO—SiO_2—Al_2O_3$, $MgO—SiO_2—ZnO$, $MgO—SiO_2—ZrO_2$, $MgO—SiO_2—CuO$, $MgO—SiO_2—CaO$, $MgO—SiO_2—Fe_2O_3$, $MgO—SiO_2—B_2O_3$, $MgO—SiO_2—WO_3$, $MgO—SiO_2—Na_2O$, $MgO—SiO_2—Ga_2O_3$, $MgO—SiO_2—La_2O_3$, $MgO—SiO_2—Nb_2O_5$, $MgO—SiO_2—Mn_2O_3$, $MgO—SiO_2—Co_3O_4$, $MgO—SiO_2—NiO$, $MgO—SiO_2—PbO$, $MgO—SiO_2—Bi_2O_3$, $MgO—Al_2O_3—ZnO$, $MgO—Al_2O_3—ZrO_2$, $MgO—Al_2O_3—Fe_2O_3$, $MgO—Al_2O_3—WO_3$, $MgO—Al_2O_3—La_2O_3$, $MgO—Al_2O_3—Co_3O_4$, $CaO—SiO_2—Al_2O_3$, $CaO—SiO_2—SnO$, $CaO—SiO_2—Nb_2O_5$, $CaO—SiO_2—WO_3$, $CaO—SiO_2—TiO_2$, $CaO—SiO_2—MoO_3$, $CaO—SiO_2—HfO_2$, $CaO—SiO_2—Ta_2O_5$, $CaO—Al_2O_3—SiO_2$, $CaO—Al_2O_3—PbO$, $CaO—Al_2O_3—Nb_2O_5$, $CaO—Al_2O_3—WO_3$, $CaO—Al_2O_3—TiO_2$, $CaO—Al_2O_3—MoO_3$, $CaO—HfO_2—Al_2O_3$, $CaO—HfO_2—TiO_2$, and the like. Other suitable mixed metal oxides embraced within the scope of this invention are disclosed by Tanabe et al., Bulletin of the Chemical Society of Japan, Vol. 47(5), pp. 1064–1066 (1974).

The mixed metal oxides described herein which can be used as catalysts may contribute to product selectivity and/or catalytic activity of the reaction and/or stability of the catalyst. As discussed hereinafter, the metal oxide catalyst employed in this invention may also contain support(s), binding agent(s) or other additives to stabilize or otherwise help in the manufacture of the catalyst.

The catalysts which comprise two or more metal oxides may be prepared in a wide variety of ways. For example, the two or more metal oxides can be provided from metal salts which can either be heated or precipitated to form the mixed metal oxides. Also, two or more metal oxides may be provided as a partial condensate on a support, such as a silica or alpha, beta or gamma alumina, silicon carbide, and the like, and then condensed by heating to effect polymerization to the desired oxide form. The two or more metal oxides may be condensed from hydrolyzable monomers to the desired oxides, indeed, to form oxide powders which can thereafter be compressed in the presence of a condensation catalyst to form pellets and larger structures of the mixed metal oxide catalyst. A blend of the powders and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the mixed metal oxide catalyst to the support.

In an embodiment of this invention, a magnesium salt, e.g., magnesium nitrate, and an aluminum salt, e.g., aluminum nitrate, are precipitated using ammonium hydroxide. The material is then washed with deionized water and calcined at a temperature of from about 350° C. to about 450° C. to afford the desired magnesium:aluminum mixed metal oxide catalyst.

In another embodiment, a magnesium oxide, e.g., magnesium carbonate hydroxide pentahydrate, and an aluminum oxide, e.g., aluminum hydroxide hydrate, are added to deionized water and thoroughly mixed to form a paste. The paste is then calcined at a temperature of from about 350° C. to about 450° C. to afford the desired magnesium:aluminum mixed metal oxide catalyst.

A preferred catalyst structure comprises a Group IIA and IIIA mixed metal oxide having a surface area of at least about 100 m$^2$/gm which may or may not be bonded to a support material. The metal oxide catalysts on a support preferably have a surface area greater than about 20 m$^2$/gm to as high as about 260 m$^2$/gm, or greater depending upon which metal oxides are employed. In the case of magnesium:aluminum oxides, the surface area can be greater than about 50 m$^2$/gm to as high as about 260 m$^2$/gm, more preferably, greater than about 100 m$^2$/gm to as high as about 260 m$^2$/gm, determined according to the single point N$_2$ method.

The term "support," as used herein and in the claims, means a solid structure which does not adversely affect the catalytic properties of the catalyst and is at least as stable as the catalyst to the reaction medium. The support can function as a catalyst independent of the mixed metal oxide catalyst used herein, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the mixed metal oxides. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the metal oxide catalyst by virtue of a binding medium.

The support may constitute a separate phase in the process of extruding the catalytic structure. In this embodiment, the support forming material, preferably as a paste is blended with a paste of the metal oxide catalyst or a partial condensate thereof. The paste may comprise the oxide forms of the support and the metal oxide catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the mixed metal oxide catalyst.

A preferred group of mixed metal oxide catalysts for use in this invention include materials having the formula:

$$M_x^{2+}Q_y^{3+}(OH)_{2x+3y-nz}A_z^{n-} \cdot a \, H_2O \qquad (I)$$

wherein M is at least one divalent metal cation; Q is at least one trivalent metal cation; and A is at least one anion providing a valence (n−), wherein n is at least 1, e.g., between 1 and 4 and most often between 1 and 3, and wherein a is a positive number, M, Q, and A are provided in a proportion such that x/y is a number equal to or greater than 1, z has a value greater than zero and $2x+3y-nz$ is a positive number. M, Q and A may be selected to provide a layered structure. Preferably, x/y is in the range of 1 to 12, more preferably x/y is in the range of 1 to 6 and most preferably is in the range of 1 to 4. Preferably, z has a value such that x/z is between n and 12n, more preferably between n and 6n and most preferably between n and 4n.

Suitable divalent metal cations, M, broadly include elements selected from the Transition elements and Groups IIA and IVA of the Periodic Table as well as certain Group IIIB elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, strontium and copper. Suitable trivalent metal cations, Q, broadly include elements selected from the Transition elements and Groups IIIA and VA of the Periodic Table as well as certain Group IIIB elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, boron, gallium and lanthanum.

The composition of formula (I) also can include a wide range of anions, A. Any anion or combination of anions which can balance the charge of the cations can be used. Suitable anions include inter alia. halides (such as chloride, fluoride, bromide, and iodide), nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, as well as organic anions such as oxalate, acetate, hexanoate, sebacate, formate, benzoate, malonate, lactate, oleate, salicylate, stearate, citrate, tartrate, maleate, and the like. The class of metalate anions described in U.S. Pat. No. 4,667,045, including metavanadate, orthovanadate, molybdate, tungstate, hydrogen pyrovanadate and pyrovanadate, also are suitable as anion A. Anions suitable for use in combination with the metal cations previously identified as being particularly suitable are carbonate, halide, phosphate, chromate, sulfate, hydroxide, oxalate, acetate, nitrate, hexanoate, sebacate, vanadate, molybdate, tungstate and ferrocyanate.

The foregoing lists of suitable divalent and trivalent cations and suitable anions are meant to be illustrative and not exclusive. Those skilled in the art will recognize that other cations and anions can be used provided that the specific type of cations and their relative amounts (x/y ratio) and the specific type of anions and their relative amount result in a mixed metal oxide composition.

Included in the materials identified above are those based on exchangeable anionic clay minerals. For example, compositions of formula (I) wherein M is magnesium and Q is aluminum are related to hydrotalcites, while compositions in which M is nickel and A is aluminum are related to takovites. In fact, mixed metal oxides prepared using magnesium, nickel or cobalt as the divalent cation and aluminum as the trivalent cation exhibit the typical X-ray diffraction pattern of a hydrotalcite.

In another preferred aspect, the processes of this invention can utilize mixed metal oxide catalyst compositions prepared by calcining at an elevated temperature compositions according to formula (I). Suitable calcined compositions have the general formula:

$$M_x^{2+}Q_y^{3+}(O)_{(2x+3y-nz)/2}D_z^{n-} \qquad (II)$$

wherein M, Q, x, y, z and n have the same meanings defined above in connection with formula (I), and D is at least one nonvolatile anion. Nonvolatile anions may include, inter alia. halides, nitrates, phosphites, phosphate, vanadate, molybdate, tungstate, sulfite, sulfate, chromate, arsenate, borate, chlorate and the like. This list is illustrative and not exclusive.

Heat treating the formula (I) compositions to prepare the calcined mixed metal oxide compositions of formula (II) can be done, for example, at a temperature in the range of 200° C. to 800° C. for a period of time of about 12 to 24 hours under an inert atmosphere such as nitrogen or in appropriate cases under an oxidizing atmosphere such as air.

Calcination of the mixed metal oxide composition dehydrates the composition and converts at least partially the metal hydroxides to metal oxides. Any nonvolatile anions may be present in the calcined material.

Provided the calcination temperature is not excessive, the mixed metal oxide can be rehydrated to the mixed metal hydroxide with water. Generally, the mixed metal oxide can be restored readily if the calcination temperature does not exceed about 600° C. Mixed metal oxides which are calcined under more severe conditions are not easily rehydrated and lower surface area materials are obtained.

Certain compositions falling within formula (I), such as hydrotalcite, which comprises a magnesium-aluminum hydroxide carbonate, and takovite, which comprises a nickel-aluminum hydroxide carbonate, are naturally occurring compositions. However, such compounds, as well as their related compositions, also can be prepared synthetically from inexpensive starting materials using well-known coprecipitation techniques. Procedures for direct synthesis of such materials are described in Itaya et al., *Inorg. Chem* (1987) 26:624–626; Taylor, R. M., *Clay Minerals* (1984) 19:591–603; Reichle, U.S. Pat. No. 4,476,324; Bish, D. L., *Bull. Mineral* (1980), 103:170–175 and Miyata et al., *Clays and Clay Minerals* (1977), 25:14–18. Using direct synthesis one has the ability to vary within wide limits the $M^{+2}/Q^{+3}$ atomic ratio as well as the anion.

For example, a composition of formula (I) $M^{+2}$ is nickel or magnesium, $Q^{+3}$ is aluminum and $A^{n-}$ is carbonate can be prepared by adding, as aqueous solutions, (a) a mixture of nitrates, sulfates or chlorides of nickel or magnesium and aluminum in a desired atomic ratio of nickel or magnesium to aluminum, e.g. 6 atoms of nickel as nickel chloride to 2 atoms of aluminum as aluminum chloride, to (b) an aqueous solution of a stoichiometric amount of sodium hydroxide and a water soluble salt of the desired anion, e.g., sodium carbonate. The two solutions are mixed at a temperature of about 25° C. to 35° C. with vigorous stirring over a several-hour period to produce a slurry. The slurry then is heated for about 18 hours at a temperature within the range of about 50° C. to 200° C. (preferably between about 60° C. to 75° C.) in order to control crystallization and the ultimate particle size of the resulting crystals. After filtering, and thorough washing and drying, the solids are recovered, typically as a powder.

As noted above, this procedure can be adapted to a wide variety of cations, cation atomic ratios and anion substitutions. For example, water soluble salts of divalent magnesium, cobalt, zinc, copper, iron and calcium can be substituted for the nickel chloride illustrated above, while water soluble salts of trivalent gallium and lanthanum can replace the aluminum chloride. A wide variety of other combinations also will be apparent to those skilled in the art. Generally, the rate of metal ion addition to the aqueous caustic/anion solution is not critical and can be varied widely. For example, a preferred preparation method is described in Schaper, H. et al., *Applied Catalysis*, 54, 1989, 79–90, the disclosure of which is incorporated herein by reference. The reaction temperature also is not critical, although the temperature during the reaction preferably is kept below about 100° C. An important feature of the procedure is the use of efficient agitation during the mixing procedure to avoid the formation of undesired by-products.

Loading of an anion A or D into the mixed metal oxide compositions is influenced by a variety of factors including (i) the amount of anion used in the preparation relative to the metal cations, (ii) the atomic ratio of the metal cations (x/y) in the preparation procedure, (iii) the size of the cations and anions and (iv) the preparation procedure. As used herein, "loading" is defined as the amount of available valences provided by a desired anion A or D expressed as a percentage of the total available valences for anion A or D. For example, carbonate loading in a hydrotalcite-type catalyst can be maximized by (i) using an excess (e.g., a greater than 3:1 molar ratio) of sodium carbonate to aluminum chloride during catalyst preparation and (2) adjusting the atomic ratio of magnesium to aluminum cations to about 2:1.

Mixed metal oxide compositions suitable as catalysts also can be prepared from the native or synthetic hydrotalcite-type compositions by ion exchange. For example, hydrotalcite can be treated at ambient conditions with 0.01N phosphoric acid for about 18 hours to replace the carbonate anion with phosphate anion. A halide analog of hydrotalcite prepared directly or by anion-exchange could be contacted with molybdic acid or a water soluble salt thereof, or with a water soluble salt of tungstic acid or vanadic acid in order to substitute the transition metal anion for the halide anion in the catalyst structure thereby to produce a mixed metal oxide composition of formula (I). Other ion exchanges will be apparent to those skilled in the art.

Calcined mixed metal oxide compositions may exhibit a higher level of selectivity/activity than uncalcined compositions. If a calcined mixed metal oxide catalyst composition experiences any decline in selectivity, it can be regenerated by a heat treatment in the presence of air to restore at least a portion of its initial level of selectivity/activity enhancement and reused. Conditions discussed above for calcining the hydrated mixed metal oxide compositions are suitable for regenerating compositions which have experienced a decline in activity.

Catalysts having the formulas (I) and (II) above wherein M is at least one of magnesium and calcium, Q is aluminum or gallium, A is at least one of carbonate, bicarbonate, phosphate, sulfate and nitrate, x/y is between 1 and 20, z has a value which satisfies the relationship: x/z is between n and 12n, and a is a positive number, are generally preferred for vapor phase decarboxylation due to their combination of activity (conversion of precursor) and selectivity. A preferred process involves a vapor phase process using mixed metal oxide catalyst wherein $M^{2+}$ is magnesium, $Q^{3+}$ is aluminum, $A^{n-}$ is carbonate, x/y is about 1, and z is about 1.

A group of preferred mixed metal oxide catalyst compositions which can be employed in the processes of this invention is disclosed in copending U.S. patent application Ser. No. 125,134, filed Nov. 25, 1987, the disclosure of which is incorporated herein by reference.

The step (ii) reaction may be effected in the liquid or vapor or supercritical liquid states or mixtures thereof. In this context, the vapor phase reaction is intended to refer to the general vapor state of the starting materials. Though the step (ii) reaction conditions may range from subatmospheric or atmospheric to superatmospheric conditions, it is desirable to run the step (ii) reaction from about 1 mm Hg to about 5,000 mm Hg, preferably from about 100 mm Hg to about 2,500 mm Hg.

The temperature of the step (ii) reaction may be as low as about 150° C. to about 500° C. Preferably, the reaction temperature ranges from about 175° C. to about 375° C., and most preferably from about 225° C. to about 350° C.

Suitable carboxylated N-monosubstituted nitrogen-containing compounds and carboxylated N,N-disubstituted nitrogen-containing compounds for use in the step (ii) reaction can be prepared by the step (i) transesterification reaction or by other methods such as the carbonylation of nitrogen-containing compounds with carbon monoxide and oxygen at elevated temperatures in the presence of certain copper salts. Such a carbonylation process can be an alternative to the step (i) transesterification reaction and is encompassed within the generic scope of this invention. It is also appreciated that two or more $CO_2$ synthons can be reacted under conditions effective to produce a carboxylated N-monosubstituted nitrogen-containing compound or a carboxylated N,N-disubstituted nitrogen-containing compound.

The step (ii) reaction can be conducted in the presence of an inert diluent which can be either a liquid or gas. When a liquid diluent is employed, it should preferably be a good solvent for the starting materials, inert under the reaction conditions, and of such a nature that separation from the nitrogen-containing compound product will not be difficult. For instance, the boiling points of the diluent and the nitrogen-containing compound product should differ by an adequate amount and there should be no tendency of the diluent to form an azeotrope with the desired nitrogen-containing compound product.

Examples of useful liquid diluents that meet the foregoing qualifications include benzene, toluene, xylene, ethylbenzene, anisole, heptane, octane, nonane, decane, dibutyl ether, and the like. Hydrocarbons are preferred.

Illustrative gaseous diluents include for example, nitrogen, methane, hydrogen, carbon monoxide or carbon dioxide. The gaseous diluent should of course be chosen so that it does not prevent the preparation of the desired products.

While the use of such diluents may be beneficial, the processes of this invention can be operated using pure starting material(s) as a liquid or gaseous feed. The degree of dilution of the starting materials with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

For processes of this invention in which a carboxylated N-monosubstituted nitrogen-containing compound or a carboxylated N,N-disubstituted nitrogen-containing compound is contacted with a mixed metal oxide catalyst under conditions effective to produce a nitrogen-containing compound or ammonia or a N-monosubstituted nitrogen-containing compound and a $CO_2$ synthon are contacted in the presence of a mixed metal oxide catalyst under conditions effective to produce a nitrogen-containing compound or other related processes described herein, it is understood that the process conditions described herein for the step (ii) decarboxylation reaction can desirably be employed for such processes.

The processes of this invention are useful for preparing substituted and unsubstituted nitrogen-containing compounds such as those embraced by the formulae $R_1NH_2$, $R_2NH_2$, $RNHR_1$, $RNHR_2$ or $RNCO$ wherein $R$, $R_1$ and $R_2$ are as defined above. It is understood that the R and $R_1$ substituents together and the R and $R_2$ substituents together can complete a heterocycloalkyl ring which can be substituted or unsubstituted. Illustrative nitrogen-containing compounds prepared by the processes of this invention include, for example, methylamine, dimethylamine, methyl isocyanate, ethylamine, diethylamine, cyclohexylamine, isopropylamine, diisopropylamine, phenyl isocyanate, monoisopropanolamine, monethanolamine, ethylenediamine and the like.

The nitrogen-containing compound products produced by the processes of this invention can be separated by distillation. For example, a crude reaction product can be subjected to a distillation-separation at atmospheric or reduced pressure through a packed distillation column. Reactive distillation may be useful in conducting the step (i) transesterification reaction.

The processes of this invention may be carried out using, for example, a fixed bed reactor, a fluid bed reactor, or a slurry reactor. The optimum size and shape of the catalyst will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the mixed metal oxide catalyst. When complete conversion is not desired or not obtainable, the starting materials can be separated from the nitrogen-containing compound product, for example by distillation, and the starting materials then recycled back into the reaction zone.

The processes are conducted for a period of time sufficient to produce the nitrogen-containing compound products. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Illustrative of suitable reactants in effecting the processes of this invention include by way of example:
AM—ammonia
EC—ethylene carbonate
PC—propylene carbonate
DMC—dimethyl carbonate
UR—urea
DPC—diphenyl carbonate
DEC—diethyl carbonate
MA—methylamine
EA—ethylamine EDA—ethylenediamine
MEA—monoethanolamine
MCA—methyl carbamate
ECA—ethyl carbamate
MMCA—methyl N-methyl carbamate
EECA—ethyl N-ethyl carbamate Illustrative of suitable products prepared by the processes of this invention include by way of example:
MIPA—monoisopropanolamine
DIPA—diisopropylamine
MEA—monoethanolamine
MA—methylamine
IPA—isopropylamine
MIC—methyl isocyanate
PIC—phenyl isocyanate
EA—ethylamine
EDA—ethylenediamine
DMA—dimethylamine
DEA—diethylamine
CHA—cyclohexylamine Illustrative of permissible reactions encompassed within the scope of this invention include, for example, the following reactant/product combinations:

| REACTANT(S) | PRODUCT(S) |
| --- | --- |
| AM, PC | MIPA |
| AM, EC | MEA |
| AM, DMC | MA |
| MA, DMC | DMA |
| MA, DPC | MIC |
| MEA, UR | EDA |
| AM, DEC | EA |
| EA, DEC | DEA |

As used herein, the phrase "residue of an organic compound" is contemplated to include all permissible residues of organic compounds. In a broad aspect, the permissible residues include acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, alkyl(oxyalkylene), aryl(oxyalkylene), cycloalkyl(oxyalkylene), heterocycloalkyl(oxyalkylene), hydroxyalkyl, hydroxyalkyl(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

What is claimed is:

1. A process for preparing N-monosubstituted or N,N-disubstituted amines which comprises contacting a carbamate having the formula:

$$H_2N(C(O)OR_1) \text{ or } RHN(C(O)OR_1)$$

wherein R is the residue of an organic compound and $R_1$ is the residue of an organic compound, with a mixed metal oxide catalyst under decarboxylation conditions effective to produce the corresponding N-monosubstituted or N,N-disubstituted amine.

2. The process of claim 1 wherein the carbamate is methyl carbamate, ethyl carbamate or isopropyl carbamate.

3. The process of claim 1 wherein the carbamate is methyl N-ethyl carbamate or ethyl N-ethyl carbamate.

4. The process of claim 1 wherein the mixed metal oxide catalyst comprises two or more Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

5. The process of claim 4 wherein the oxide catalyst comprises two or more oxides of magnesium, aluminum, calcium, strontium, gallium, beryllium, barium, scandium, yttrium, lanthanum, cerium, gadolinium, terbium, dysprosium, holmium, erbium, thulium, butecium, ytterbium, niobium, tantalum, chromium, molybdenum, tungsten, titanium, zirconium, hafnium, vanadium, iron, cobalt, nickel, zinc, silver, cadmium, boron, indium, germanium, tin, lead, arsenic, antimony and bismuth.

6. The process of claim 1 wherein the mixed metal oxide catalyst comprises at least one Group IIA metal oxide.

7. The process of claim 1 wherein the mixed metal oxide catalyst comprises a Group IIA metal oxide and a Group IIIA metal oxide.

8. The process of claim 1 wherein the mixed metal oxide catalyst comprises a Group IIA metal oxide and a Group IIIB metal oxide.

9. The process of claim 1 wherein the mixed metal oxide catalyst comprises magnesium oxide and aluminum oxide.

10. The process of claim 1 wherein the mixed metal oxide catalyst comprises a high surface area mixed metal oxide.

11. The process of claim 1 wherein the mixed metal oxide catalyst has a surface area greater than about 50 $m^2/gm$.

12. The process of claim 6 wherein the Group IIA metal oxide comprises from about 10 weight percent to about 90 weight percent of the weight of the catalyst.

13. The process of claim 1 wherein the mixed metal oxide catalyst is associated with a support material.

14. The process of claim 13 wherein the support comprises an alumina material or an alumina-silica material.

15. The process of claim 13 wherein the support comprises an silica material or a silica-alumina material.

16. The process of claim 13 wherein the support comprises from about 2 to about 50 percent by weight of the mixed metal oxide catalyst.

17. The process of claim 1 wherein the mixed metal oxide catalyst comprises:
(a) a material having the formula:

$$M_x{}^{2+}Q_y{}^{3+}(OH)_{2x+3y-nz}A_z{}^{n-} \cdot a\, H_2O \qquad (I)$$

wherein M is at least one divalent metal cation; Q is at least one trivalent metal cation; and A is at least one anion providing a valence (n−), wherein n is 1 to 4 and wherein a is a positive number, M, Q and A are provided in a proportion such that x/y is a number equal to or greater than 1, z has a value greater than zero and 2x+3y-nz is a positive number, or (b) a material prepared by calcining the material of formula (I) having the formula $$M_x{}^{2+}Q_y{}^{3+}(O)_{(2x+3y-nz)/2}D_z{}^{n-} \qquad (II)$$

wherein M, Q, x, y, z and n have the same meanings defined above in connection with formula (I), and D is at least one nonvolatile anion.

18. The process of claim 17 wherein x/y is a number between 1 and 12 and z has a value which satisfies the relationship: x/z is between n and 12n.

19. The process of claim 17 wherein A is selected from the group consisting of carbonate, halide, phosphite, phosphate, chromate, sulfate, hydroxide, oxalate, acetate, nitrate, hexanoate, sebacate, vanadate, molybdate, tungstate and ferrocyanate.

20. The process of claim 17 wherein D is selected from the group consisting of halides, phosphite, phosphate, vanadate, molybdate, tungstate, sulfite, sulfate, chromate, arsenate, borate and chlorate.

21. The process of claim 17 wherein x/y is a number between 1 and 6 and z has a value which satisfies the relationship: x/z is between n and 6n.

22. The process of claim 17 wherein said material prepared by calcining the material of formula (I) has been heat treated at a temperature in the range of 200° C. to 800° C. for 12 to 24 hours.

23. The process of claim 17 wherein M is magnesium and and Q is aluminum.

24. The process of claim 1 wherein the N-monosubstituted amine is a material having the formula:

$$R_1NH_2$$

wherein $R_1$ is the residue of an organic compound.

25. The process of claim 1 wherein the N,N-disubstituted amine is a material having the formula:

$$RNHR_1$$

wherein R is the residue of an organic compound.

26. The process of claim 1 wherein the N-monosubstituted or N,N-disubstituted amine is methylamine, dimethylamine, ethylamine, diethylamine, cyclohexylamine, isopropylamine, diisopropylamine, ethylenediamine, monoethanolamine or monoisopropanolamine.

* * * * *